(12) United States Patent
McMinn

(10) Patent No.: US 8,172,850 B2
(45) Date of Patent: May 8, 2012

(54) ALIGNMENT DEVICE

(76) Inventor: Derek James Wallace McMinn, Stourbridge (GB)

( * ) Notice: Subject to any disclaimer, the term of this patent is extended or adjusted under 35 U.S.C. 154(b) by 1017 days.

(21) Appl. No.: 12/108,218

(22) Filed: Apr. 23, 2008

(65) Prior Publication Data

US 2008/0269757 A1    Oct. 30, 2008

(30) Foreign Application Priority Data

Apr. 26, 2007   (GB) .................................. 0708111.0

(51) Int. Cl.
*A61B 17/58* (2006.01)
*A61B 17/60* (2006.01)
*A61F 2/00* (2006.01)

(52) U.S. Cl. ........................................................ 606/91
(58) Field of Classification Search .................... 606/87, 606/91, 99
See application file for complete search history.

(56) References Cited

U.S. PATENT DOCUMENTS

| | | | |
|---|---|---|---|
| 4,955,891 A * | 9/1990 | Carol | 606/130 |
| 5,141,512 A * | 8/1992 | Farmer et al. | 606/87 |
| 5,658,294 A | 8/1997 | Sederholm | |
| 2004/0210233 A1 | 10/2004 | Yoon et al. | |

FOREIGN PATENT DOCUMENTS

| | | |
|---|---|---|
| GB | 2224937 A | 5/1990 |
| GB | 2268688 A | 1/1994 |
| GB | 2288763 | 11/1995 |
| WO | WO-2005/009303 A1 | 2/2005 |
| WO | WO-2006/109983 A1 | 10/2006 |

OTHER PUBLICATIONS

Search Report for GB patent application GB0708111.1 (Issued Aug. 4, 2008).

* cited by examiner

*Primary Examiner* — Thomas C. Barrett
*Assistant Examiner* — Sameh Boles
(74) *Attorney, Agent, or Firm* — Bingham McCutchen LLP

(57) ABSTRACT

An alignment device comprises a guide having a tangible guide component, said guide being configured for arranging the guide component at an angle with respect to a reference element; and a positioning means; the positioning means and the guide component being operable to cooperate to position an item at the angle set by the guide component. The alignment device is particularly useful in surgical procedures for the alignment of surgical tools and implants.

14 Claims, 7 Drawing Sheets

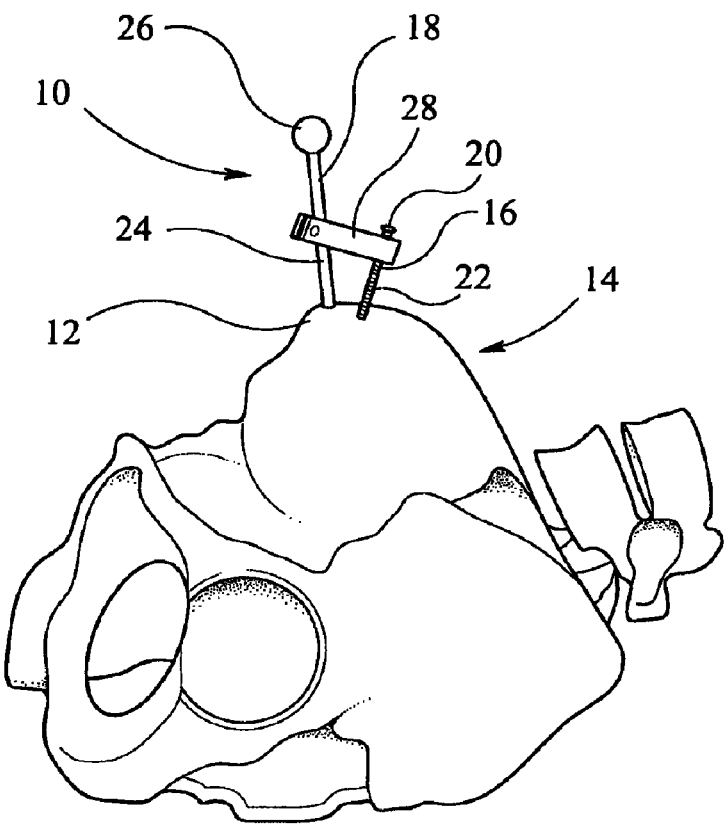
FIG 1A
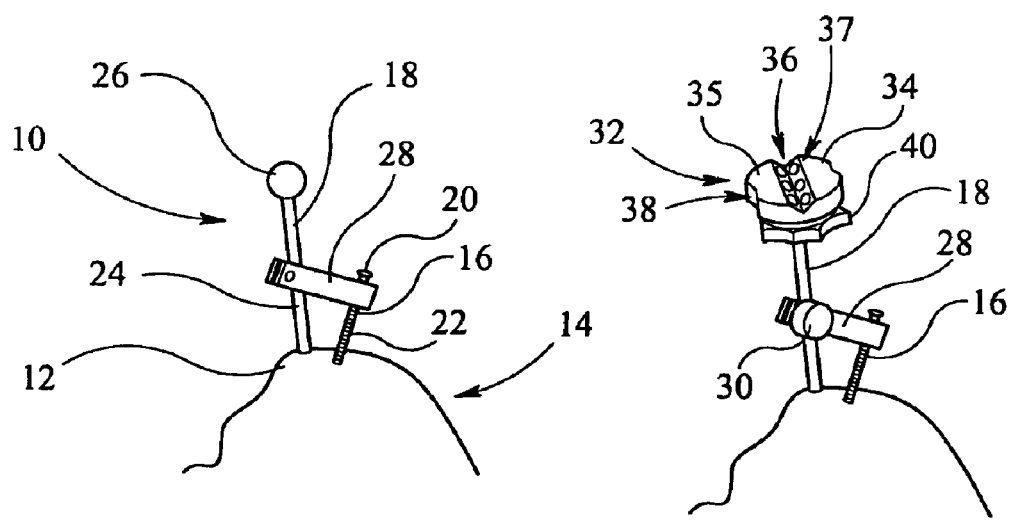
FIG 1B
FIG 2

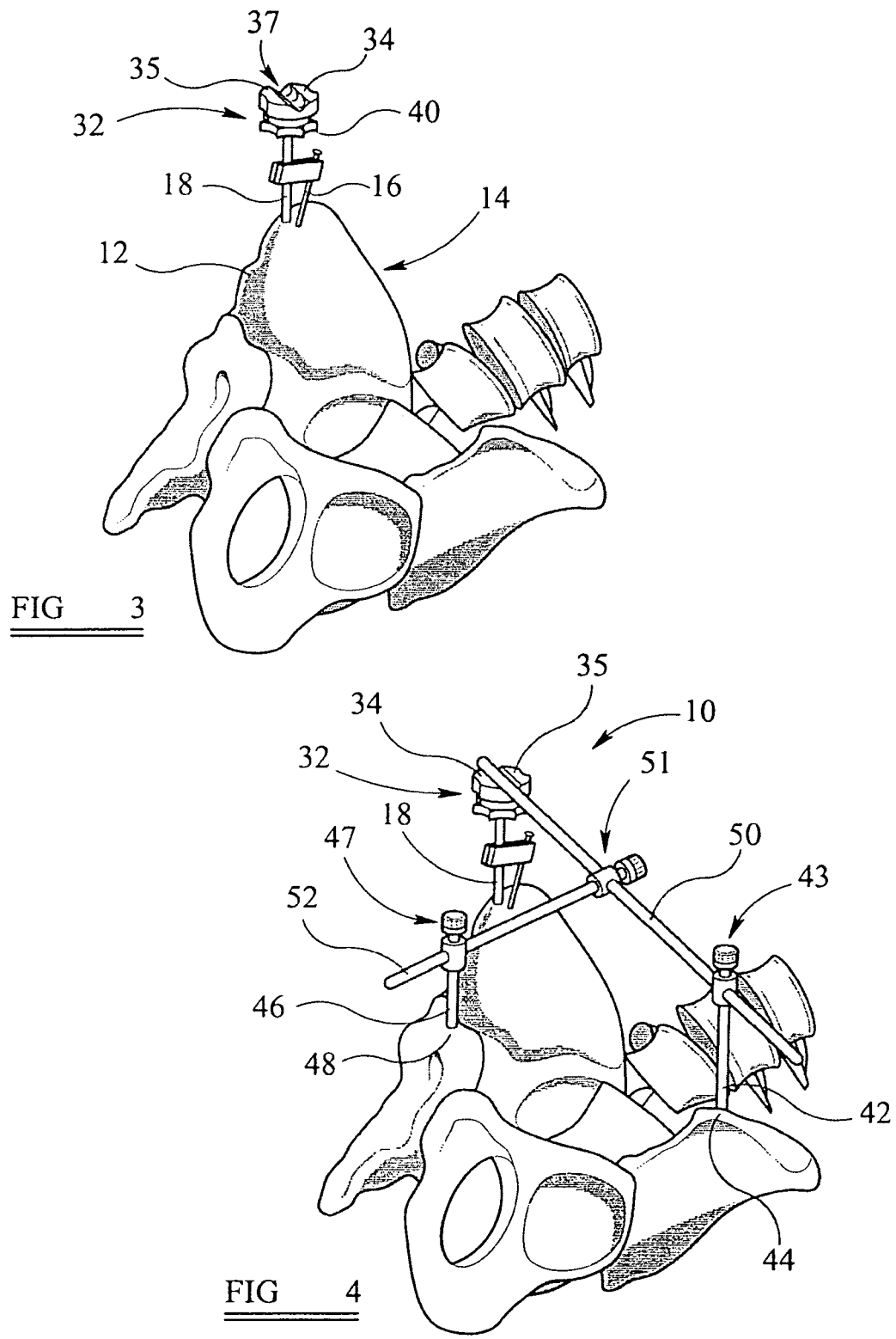

ALIGNMENT DEVICE

CROSS-REFERENCE TO RELATED APPLICATIONS

This application claims priority to and the benefit of United Kingdom patent application Serial No. 0708111.0, filed Apr. 26, 2007, the disclosure of which is incorporated herein by reference in its entirety.

FIELD OF THE INVENTION

This invention relates to an alignment device. Particularly, but not exclusively, the invention relates to an alignment device that is suitable for the alignment of tools and implants during surgery.

BACKGROUND TO THE INVENTION

During most cases of hip arthroplasty, both bearing elements of the ball and socket joint are replaced with manufactured implants in the form of an acetabular component and a femoral component. There are various designs of these components and they may be manufactured in various materials, have various combinations of geometry and be implanted and fixed by various means.

The acetabular component is usually in the form of a concave partial sphere which functions as a cup or socket. It is fixed into place in a prepared acetabulum by one of a number of means. The femoral component is usually in the form of a convex partial sphere (i.e. a ball), which is fixed in place on the top of a prepared femur, also by various means. The femoral component is shaped so as to be received within the acetabular component to form the joint.

When engaged, it is preferable that the position of the centre of rotation of the bearing elements approximates the centre of rotation of the original anatomical bearing otherwise there will be an increased risk of hip dislocation. During installation of such a bearing system, it is also desirable to place the elements at such positions so as to optimise their performance. This performance may be expressed in terms of a series of factors such as longevity, amount of wear, morphology, size of wear debris, range of motion, stability in motion, and frictional torque. The relative importance of these performance factors is implant and patient specific. However, all performance factors are influenced in various degrees by the intra operative positioning of each element of the bearing—relative to each other and relative to the patient's anatomy.

With regard to total knee replacement it is known that varus positioning of the tibial component can deteriorate performance characteristics. Increased wear of the bearing, increased fracture rate of the tibial base plate and increased loosening rate of the tibial component are all recognized problems with tibial component mal-position.

A company called BrainLAB provides a particular device for use in positioning such bearing components. This device employs computer simulation and navigation software and uses multiple infrared sources and cameras to detect the position of a pointer instrument operated by a surgeon. The computer is configured to display an image of the patient's anatomy and to direct the surgeon to position the implant in the correct place. Others have also proposed use of computer-aided navigation in a similar manner to that described but involving computerised tomography (CT) or the morphing standard models. There are several drawbacks associated with such systems, including the large cost of the equipment, the complexity of the system, the time involved in the positioning procedure and the fact that it requires the surgeon to continually glance at a computer screen and therefore take his eyes away from the patient during the operation. Primarily due to the expense of the above devices, most surgeons have no option but to align tools and implants by eye. This can often lead to later complications since the positioning of such elements is uncontrolled and generally inaccurate.

It is therefore an aim of the present invention to provide an alignment device, which addresses some or all of the aforementioned problems.

SUMMARY OF THE INVENTION

According to a first aspect of the present invention there is provided an alignment device comprising a guide having a tangible guide component, said guide being configured for arranging the guide component at an angle with respect to a reference element; and a positioning means, the positioning means and the guide component being operable to cooperate to position an item at the angle set by the guide component.

Note that, in embodiments of the present invention, it may be desirable for the angle of the guide component to be set at 0° with respect to the reference element (i.e. for the guide component to be aligned with the reference element).

In a preferred embodiment, the tangible guide component and the reference element each define a plane. The guide sets the angular relationship between these two planes. The positioning means cooperates with the tangible component to facilitate positioning of the item.

An alignment device embodying the invention may be advantageously used in surgical procedures. In which case, the item to be aligned may be a surgical tool or an implant and the reference element may be a part of the patient's anatomy, for example a fixed bony point or a line or a plane defined by two or more bony points respectively.

Thus, the present invention provides a simple device that can be used to enable a surgeon to quickly and accurately align implants and tools during surgery. A surgeon, aware of the characteristics of a particular implant and patient, may therefore use the device to guide the implant into a pre-selected position relative to the patient's anatomy, so as to enhance the desired performance factor for that patient's implant.

The tangible (i.e. physical) nature of the guide component allows embodiments of the device to be formed from a purely mechanical assembly, thereby minimising manufacturing costs and permitting speedy production. Alternatively, embodiments of the device (as described below) may comprise electronic components, such as a laser pointer. However, even such electronic embodiments may be relatively cheap to produce since there is no requirement in the present invention for computer simulation and navigation software.

Due to the physical nature of the device, being a kit of mechanical and/or simple electronic parts, the complexity of the system is reduced and an alignment procedure can be carried out in a relatively short period of time. In addition, the device can be made in a relatively compact form and can be used in the vicinity of the patient so that the surgeon is not required to continually avert his eyes away from the patient during the operation.

In particular embodiments of the invention, the device may be configured for use in hip, knee, elbow or ankle replacement procedures. In the case of hip replacement, the device may be configured for aligning an acetabular component and/or a femoral component of a prosthetic hip joint.

Embodiments of the device may be configured for the alignment of surgical tools such as cutting tools, saws, reaming tools, cutting blocks and cutting guides.

In embodiments of the present invention, the guide may comprise an adjustment means for altering the set angle of the guide component. The adjustment means may include a scale for accurate setting of the angle. The adjustment means may be configured to alter the anteversion angle (i.e. the amount of forward tilt relative to a plane through the body) and/or inclination angle (i.e. the angle formed with reference to a transverse axis though the body) of the guide component. An anteversion ring, which defines an inclined surface relative to the reference element, may constitute the adjustment means. In the case of alignment of an acetabular cup, it is generally desirable to align the plane across the open face of the cup at an inclination angle of approximately 45° with reference to the transverse axis of the pelvis and an anteversion angle of approximately 20° with reference to the pelvic frontal plane defined by the 2 anterior superior iliac spines and the symphysis pubis. Thus, the inclined surface may define an anteversion angle of 20° and the anteversion ring may be rotatable relative to the reference element to set the guide component at an inclination angle of preferably 45°.

The guide may comprise a locking means to lock the angle of the guide component once it has been set.

The positioning means may be configured for attachment to an insertion tool (i.e. introducer). It may also be configured for attachment in such a manner that the positioning means and insertion tool are thereafter held in a fixed relative disposition. Alternatively, the positioning means may be integral with the insertion tool.

In one embodiment, the positioning means may comprise an extendable portion to facilitate its cooperation with the guide component. The extendable portion may be in form of telescopic components or lazy tongs.

In a particular embodiment of the invention, the guide component comprises a reflector and the positioning means comprises a laser pointer. Alternatively, the guide component comprises a laser pointer and the positioning means comprises a reflector. In either case, the said cooperation occurs when a laser beam from the laser pointer is reflected from the reflector. The reflector may be a mirror and may be made from polished stainless steel. In the case where the reflector has a planar surface, the positioning means can be configured for alignment of an item to be placed when the laser pointer is arranged perpendicularly to the reflector (i.e. when the paths of the incident laser beam and reflected laser beam are superimposed). In such an embodiment, the laser beam from the laser pointer may be configured to emanate or pass through the centre of a target configured such that the reflected laser bean may be visible on the target to indicate that the reflector and laser pointer are not appropriately aligned. The target may include markings, such as concentric circles, to indicate the amount of adjustment required in order to properly align the components.

In another embodiment, the guide component and the positioning means may each comprise planar surfaces that can be placed against each other in order to cooperate by aligning one that is free to rotate with the other which is held at a fixed angle.

The device may further comprise a datum means configured to identify at least one anatomical point as the reference element. Depending on the nature of the surgery involved and/or the type of tool or implant being positioned, the anatomical points may be points on the patient's pelvis such as the anterosuperior iliac spines and the symphysis pubis. Such points may be used to define a reference plane such as the pelvic frontal plane.

The datum means may comprise a structural framework configured for attachment to the reference element, and a datum element configured for engagement with the framework such that the datum element is aligned with the reference element. Where the reference element is the pelvic frontal plane, the framework may comprise a series of interconnecting rods. Three rods may be configured for attachment to the two anterosuperior iliac spines and the symphysis pubis, respectively. A fourth rod may be configured to extend between the two rods on the anterosuperior iliac spines to define a transverse axis. A fifth rod may be configured to link the fourth rod to the rod on the symphysis pubis. The datum element may be configured for alignment with a plane established by the fourth and fifth rods to thereby define a pelvic frontal plane. The datum element may be swivel-mounted at one end of one of the three rods so as to be adjustably moveable about a pair of orthogonal axes lying in a plane perpendicular to the axis of said one rod. The guide may be configured for attachment to the datum element to allow the guide component to be set relative to the datum element (which is representative of the reference element). In one embodiment the guide may be configured for magnetic attachment to the datum element so as to permit a sterile barrier to be incorporated therebetween.

In some embodiments of the invention, the reference element may be a pre-cut section of bone, for example, a resected femoral head.

In embodiments of the present invention, for example when the device is used in knee replacement surgery, the guide component (e.g. in the form a laser pointer) may be configured for defining an angle corresponding to the central longitudinal axis of the tibia (i.e. the reference element). The positioning means in this case (e.g. in the form of a reflector) may be attached to a cutting block at such an angle so as to correctly align the cutting block with the tibia when the guide component and the positioning means are correctly aligned (e.g. when the incident laser beam is coincident with the reflected laser beam). Alternatively, the cutting block itself may include a reflective surface that constitutes the positioning means.

As a further alternative, a cutting block or guide may not be required since a reflective saw or blade may constitute the positioning means. Accordingly, the cutting blade of a power saw could be polished to act as a reflector. Alternatively, a reflector or a laser pointer could be attached or coupled to the power saw, with a cooperating laser pointer or reflector, respectively, constituting the guide component.

Moreover, a guide component (i.e. laser pointer) may be aligned with a femoral shaft to thereby align a cutting guide or power saw incorporating a positioning means (i.e. a reflector/reflective surface) to enable an accurate distal femoral cut to be performed. This procedure avoids having to use an intramedullary rod, as traditionally employed for this type of alignment, and thereby minimises the risk of systematic fat embolisation.

The above principles may also be applied in other surgical procedures such as total elbow replacement or total ankle replacement.

According to a second aspect of the present invention, there is provided a method of alignment, comprising identifying a reference element, setting a tangible guide component at a desired angle with respect to the reference element; and operating a positioning means to cooperate with the guide component and thereby position an item at the angle set by the guide component.

BRIEF DESCRIPTION OF THE DRAWINGS

Particular embodiments of the invention will now be described, by way of example only, with reference to the accompanying drawings in which:

FIGS. 1A through 14 illustrate an alignment device according to the present invention, as it might be used in a hip replacement procedure for positioning an acetabular cup; more specifically, FIG. 1A shows a side perspective view of a pelvis and lower spine with a part of a datum means framework of an alignment device according to the present invention, attached to the right anterosuperior iliac spine;

FIG. 1B shows an enlarged view of the part of the datum means framework shown in FIG. 1A;

FIG. 2 shows a view similar to that of FIG. 1B but with a datum assembly attached, to the datum means framework;

FIG. 3 shows a view similar to that of FIG. 2A but showing the entire pelvis and lower spine;

FIG. 4 shows a view similar to that of FIG. 3 but with the remainder of the datum means framework in place on the pelvis;

FIG. 5 shows a view similar to that of FIG. 3 but illustrated from the opposite side of the pelvis;

FIG. 6 shows an enlarged view of a guide assembly attached to the datum assembly illustrated previously along with an alternative guide part shown separately for clarity;

FIG. 7 shows the assembly of FIG. 6 as attached to a pelvis and with a guide component emanating from the guide assembly;

FIG. 8 shows an exploded view of a positioning means of an alignment device according to the present invention;

FIG. 9 shows an assembled view of the positioning means of FIG. 8;

FIG. 10 shows a perspective view of an acetabular cup introducer;

FIG. 11 shows a view similar to that of FIG. 10 but with the positioning means of FIG. 9 and an acetabular cup attached thereto;

FIG. 12 shows a view similar to that of FIG. 7 but with the assembly of FIG. 11 being employed to position the acetabular cup in the appropriate place using the alignment device of the present invention;

FIG. 13 shows a partial side cross-sectional view illustrating the interface between the datum assembly and the guide assembly; and FIG. 14 shows an exploded view illustrating some of the components employed in the alignment device illustrated in the previous drawings.

DETAILED DESCRIPTION OF CERTAIN EMBODIMENTS

Figure 5:
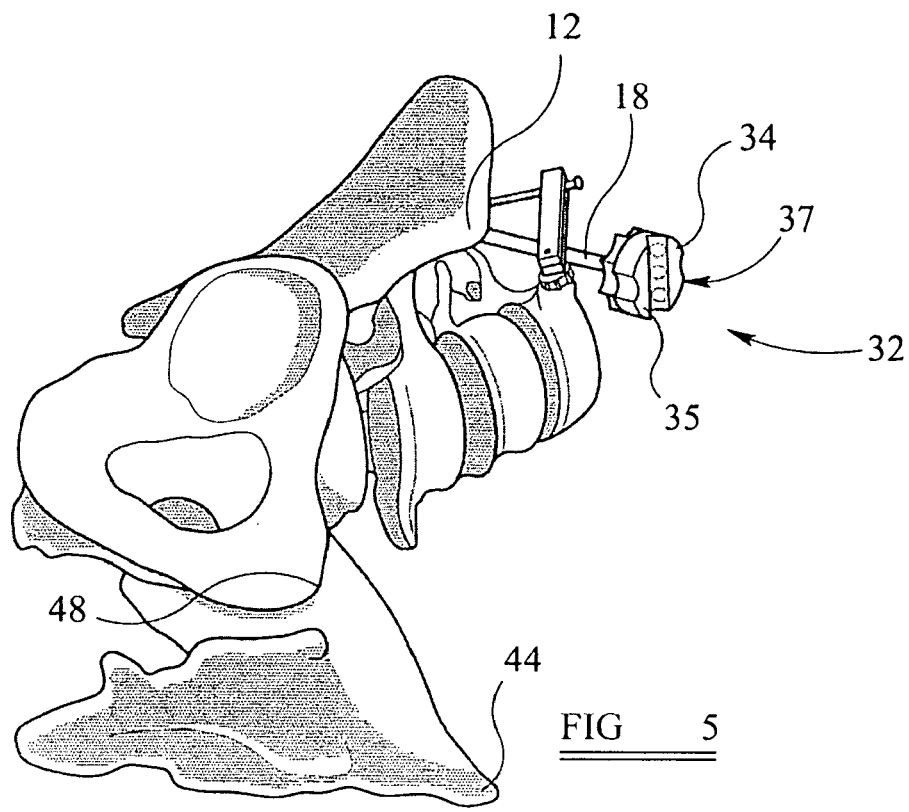

With reference to FIGS. 1A to 14, there is illustrated an alignment device according to the present invention. The various parts of the alignment device will be described in the order in which they are likely to be used during an alignment procedure. In the example illustrated, the alignment device is employed to align an acetabular cup during a hip replacement operation.

As shown in FIGS. 1A and 1B, a part of a datum means framework 10 of an alignment device according to the present invention, is attached to the right anterosuperior iliac spine 12 on a patient's pelvis 14. The part of the datum means framework 10 shown comprises a bone screw 16 and a first rod 18. As illustrated more clearly in FIG. 13, the first rod 18 is a single piece comprising a smooth shaft 24 with a substantially spherical ball 26 at one end thereof. The first rod 18 has axial symmetry and is provided with an axial bore, which allows a fixing screw 19 (shown in FIG. 13) to be inserted therethrough. The end of the first rod 18 opposite to the ball 26 is positioned on the right anterosuperior iliac spine 12 such that the longitudinal axis of the first rod 18 extends perpendicularly outwardly therefrom. The fixing screw 19 is then passed through the axial bore of the first rod 18 and screwed into the right anterosuperior iliac spine 12 to provide the primary fixation mechanism for the datum means framework 10. The bone screw 16 is screwed into the pelvis 14 a short distance from the first rod 18 and at a slight angle thereto such that the screw 16 projects outwardly away from the first rod 18. The screw 16 has a head 20 and a threaded shank 22. The head 20 has a larger diameter than the shank 22. A clamp 28 is provided to link the screw 16 to the first rod 18 and thereby to clamp the first rod 18 in a fixed rotational position relative to the right anterosuperior iliac spine 12. The clamp 28 is formed from an elongate rectangular section of steel that is folded at its midpoint and punched with coincident holes through its adjacent free ends. The clamp 28 is disposed with its midpoint wrapped around the screw 16, below the head 20. Its free ends are wrapped around the midsection of the shaft 24 of the first rod 18 and are clamped in place by a nut and bolt 30 through the holes in the clamp 28 (as shown in FIG. 2). Thus, the screw 16 and the clamp 28 provide a means for preventing rotation of the first rod 18 around the primary fixing screw 19.

A datum assembly 32 is attached to the rod 18 as illustrated in FIGS. 2 and 3. Note that the datum assembly 32 may be provided already attached to the first rod 18 before any portion of the datum means framework 10 is attached to the patient. However, for clarity, the datum assembly 32 has been omitted from FIGS. 1A and 1B.

The datum assembly 32 has a swivel body 34 that includes a datum 35, which defines a reference plane. The datum 35 in this embodiment is defined by top surface 37 of the swivel body 34. The framework 10 is configured to position the reference plane into parallel alignment with a pelvic frontal plane or other anatomical plane.

The swivel body 34 is configured to rotate and tilt on the ball 26. The swivel body 34 is substantially disc shaped and includes a recessed V-shaped channel 36 across the centre of its top surface 37. The channel 36 is configured to receive a rod of the datum means framework 10, as will be described below. On either side of the channel the sides of the disc include semi-circular notches 38. The swivel body 34 may be clamped about the ball 26 by a screw thread coupling with a thumbwheel 40.

The remainder of the datum means framework 10 is attached to the pelvis 14, as shown in FIG. 4. Thus, a second rod 42 is provided on the left anterosuperior iliac spine 44 and a third rod 46 is provided on the symphysis pubis 48. A fourth rod 50 is arranged to pass perpendicularly through the top of the second rod 42 via a coupling 43 to rest in the channel 36 of the datum assembly 32. A fifth rod 52 is arranged to pass perpendicularly through the top of the third rod 46 via a coupling 47 and to perpendicularly intersect the fourth rod 50 via a coupling 51.

The ends of the first, second and third rods 18, 42 and 46 that contact the pelvis 14 define a pelvic frontal plane. The lengths of the first, second and third rods 18, 42 and 46 are such that when the ends thereof are in contact with the pelvis, the plane defined by fourth and fifth rods 50 and 52 is parallel to the pelvic frontal plane.

Figure 14:
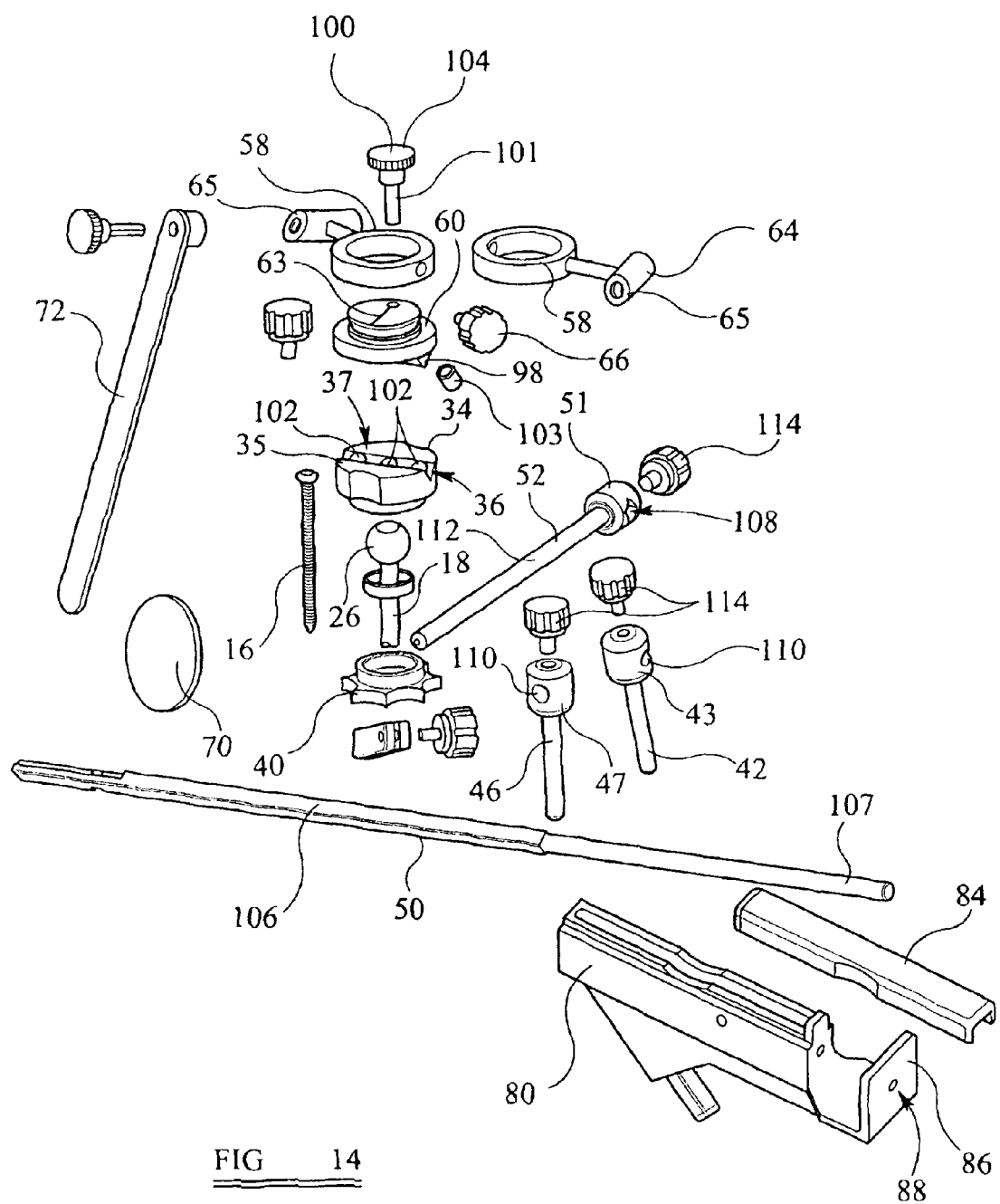

The swivel body 34 is preferably unlocked when the remainder of the datum means framework 10 is attached as described above. The end of the fourth rod 50 that rests in the channel 36 is configured to engage with the swivel body 34 in a predefined axial relationship so that rotation of the fourth rod 50, (i.e. due to the connection with the fifth rod 52) causes the swivel body 34 to rotate axially with the fourth rod 50. This is achieved, as illustrated in FIG. 14, by the fourth rod 50 being provided with a square cross-section 106 from one end to past its midpoint. One corner of the square cross-section 106 is configured to rigidly engage in the V channel 36 of the swivel body 34. The channel 36 is provided with three magnets 102 (shown in FIG. 14) which are recessed in holes along the walls of the channel 36. These magnets 102 are configured to hold the square cross-section 106 of the fourth rod 50 in place, when it is made from a cooperating material. The square cross-section 106 also fixes the rotational position of the fifth rod 52 around the axis of the fourth rod 50 since the coupling 51 on the end of the fifth rod 52 includes a square bore 108 orthogonally therethrough (shown in FIG. 14), which is configured to receive the square cross-section 106 of the fourth rod 50. Accordingly, axial rotation of the fourth rod 50 will result in corresponding axial rotation of the plane defined by the fourth and fifth rods 50, 52 and vice versa. Thus, with the datum means framework 10 in place, the swivel body 34 is positioned so that the datum 35 is in parallel alignment with the pelvic frontal plane. In other words, the datum 35 adopts the attitude of the plane defined by the three bony points. The datum assembly 32 is then locked in position by the thumbwheel 40 and the remainder of the datum means framework 10 (i.e. the second, third, fourth and fifth rods 42, 46, 50, 52) can then be removed as shown in FIG. 5.

Now that the datum assembly 32 has been locked to define an anatomical reference plane, the patient is prepared for surgery and is placed in an appropriate attitude to allow the surgeon access to the operation site. In a particular embodiment, the datum assembly 32 may be covered by drapes since the guide assembly can be configured for clamping to the datum assembly 32 via a magnetic connection. However, for ease of clarity no drapes are illustrated in this case. At this stage of the operation, the surgeon undertakes a traditional acetabular cup preparation procedure, reaching the point at which he is in a position to introduce the cup implant.

The surgeon may have an indication of desired attitude of the cup implant (i.e. the angle of the plane across face of the cup) through study of pre-operative radiographs.

Now that the reference datum 35 is established, a guide assembly 54 is coupled thereto. The purpose of the guide assembly 54 is to set a working reference plane (see A-A; B-B of FIG. 7) relative to which the surgeon can align an implant or surgical tools.

Figure 6:
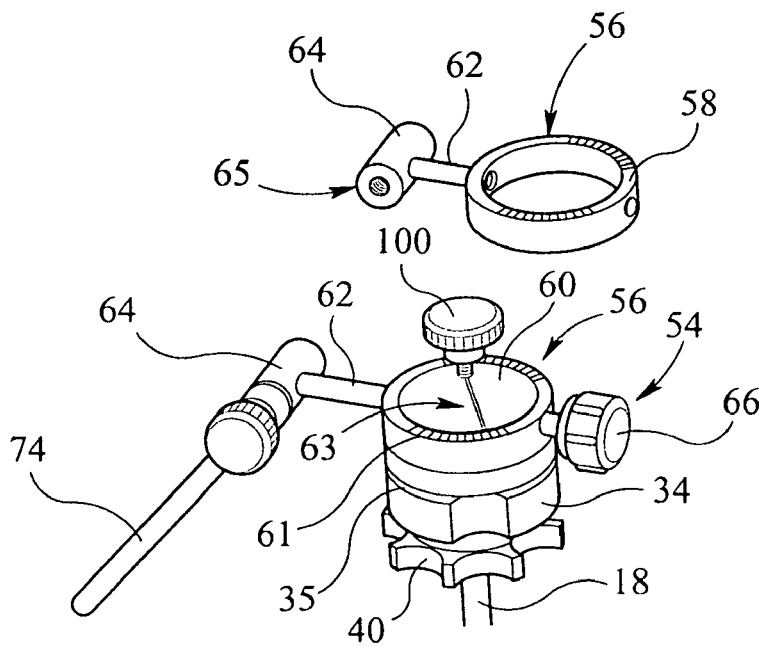
Figure 7:
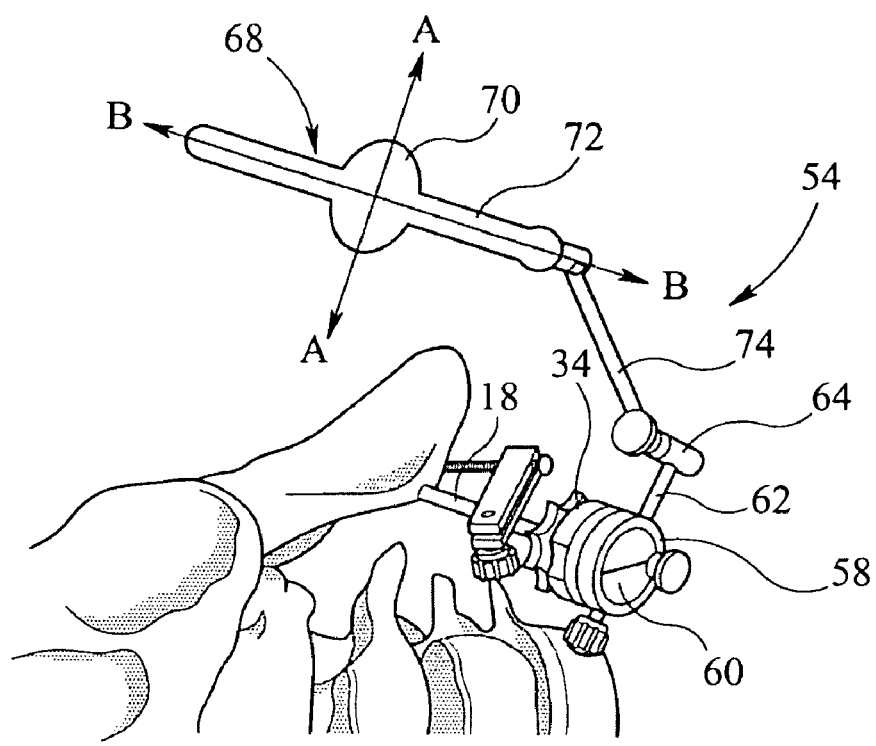

The setting of the guide assembly 54 with respect to the datum assembly 32 is illustrated in FIGS. 6 and 7. The surgeon first selects the desired radiographic anteversion by selecting an anteversion ring 56 for use in the guide assembly 54. Each anteversion ring 56 comprises an annulus 58 configured for placement over a guide marker 60 disposed on the top surface 37 of the swivel body 34 of the datum assembly 32. Extending radially from one side of the annulus 28 is a pole 62 on the end of which is mounted a cylindrical element 64. The cylindrical element 64 is mounted perpendicularly to the pole 62 with the axis of the cylindrical element 64 set parallel to the plane of the annulus 58 and therefore parallel to the plane of the datum 35. Rather than being orthogonal to the axis of the cylindrical element 64, at least one of the end planar surfaces 65 of the cylindrical element 64 is inclined. With the remainder of the guide assembly 54 attached to such an inclined planar surface 65, as will be described below, the angle of the planar surface 65 determines the anteversion angle of the guide assembly 54 relative to the datum 35. In an alternative embodiment, the angle of the axis of the cylindrical element 64 may itself set the anteversion angle relative to the plane of the annulus 58. Different anteversion rings 56 can be provided to cover a wide range of desirable anteversion angles.

Figure 13:
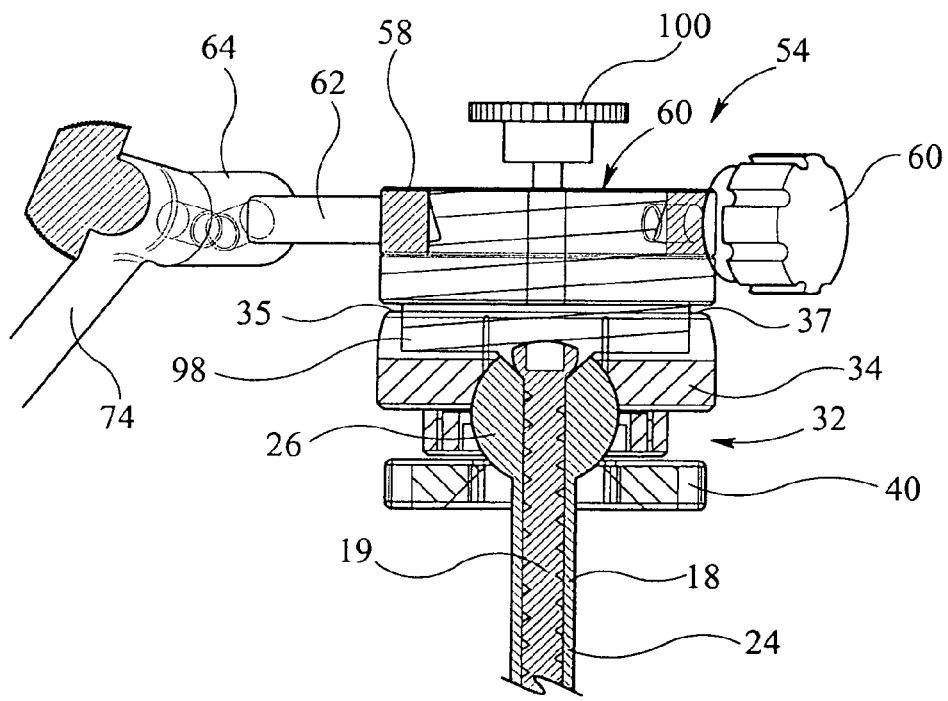

Once the desired anteversion ring 56 has been placed over the guide marker 60, the surgeon then sets the desired radiographic inclination by rotating the anteversion ring 56 about the guide marker 60 to set the inclination angle. As illustrated in FIGS. 13 and 14, in this embodiment, the guide marker 60 is a cylindrical component with an outer annular recess in its upper surface configured to allow placement of an anteversion ring 56. Its lower surface is provided with a V-shaped projection 98 that is configured for engagement in the V-shaped channel 36 in the swivel body 34 of the datum assembly 32. The magnets 102 provided in the channel 36 walls act to retain the guide marker 60 in a fixed position relative to the swivel body 34 and hence the datum 35. The use of magnets 102 also allows the guide assembly 54 to be fixed to the datum assembly 32 with a sterile barrier such as drapes provided therebetween. Accordingly, the guide assembly 54 can be attached to the datum 35 on the patient and used during the procedure without jeopardising sterility. A line is provided across the centre of the upper surface of the guide marker 60, at 90° to the axis of the V-shaped projection 98, to form a pointer 63. A screw 100 is configured to pass through a bore disposed at one end of the pointer 63. The screw 100 has a shank 101 and an enlarged head 104. The shank 101 is configured to pass through the bore and be received within one of the notches 38 on the swivel body 34 where it can be clamped by a nut 103. In such an arrangement, the head 104 of the screw 100 extends over part of the anteversion, ring 56 to thereby retain the anteversion ring 56 in rotational engagement with the guide marker 60. As illustrated in FIG. 6, each anteversion ring 56 is provided with a scale 61 thereon that is configured such that when the 0° point on the scale is aligned with the end of the pointer 63, the axis of the pole 62 is aligned with the axis of the V-shaped channel 36 which itself is aligned with the transverse axis of the pelvis (i.e. the axis previously formed by fourth rod 50). Rotation of the anteversion ring 56 about the guide marker 60 therefore results in rotation of the axis of the pole 62 relative to the transverse axis of the pelvis. Accordingly, the inclination angle of the parts of the guide assembly 54 attached to the pole 62 can be set and the resulting angle determined by the scale 61. When the desired inclination has been set, a screw 66 locks the position of the anteversion ring 56 relative to the guide marker 60. Thus, in this embodiment the anteversion ring 56 constitutes the adjustment means of the guide assembly 54.

A guide component 68 of the guide assembly 54 is attached to the cylindrical element 64, as shown in FIG. 7, either before or after the inclination angle has been set. The guide component 68 in this embodiment comprises a disc-shaped reflector 70 mounted midway along an arm 72. The arm 72 is pivotally mounted at one end to an extension 74 which itself is pivotally mounted to the inclined planar surface 65 of the cylindrical element 64. The result is that the plane A-A, B-B is, in this embodiment, parallel to the plane of the inclined planer surface 65 and therefore set at a particular anteversion angle relative to the reference plane (i.e. the plane of the datum 35). That is to say, the extension arm 74 allows the arm 72 and the reflector 70 to rotate in the plane determined by the angle of the planar surface 65 of the cylindrical element 64. As can be readily understood, the guide component 68 in the present invention is a tangible object (i.e. a physical element which can be touched) as opposed to an intangible guide such as one which is computer generated.

The guide assembly 54 is constructed such that the guide component 68 is held at the anteversion and inclination angles that have been set as hereinbefore described. Thus, the reflector 70 forms a plane at the desired angle with respect to the datum 35.

Figure 8:
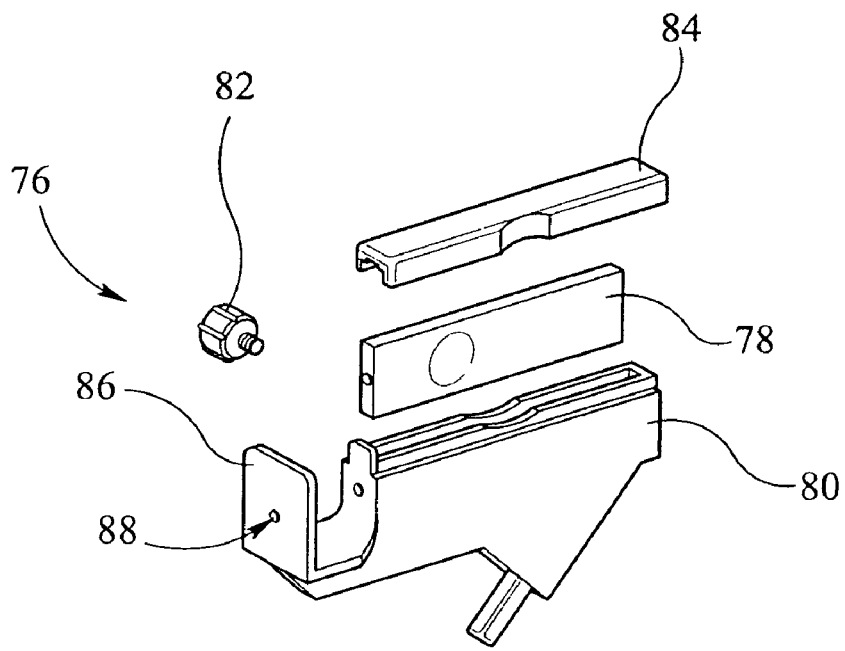
Figure 9:
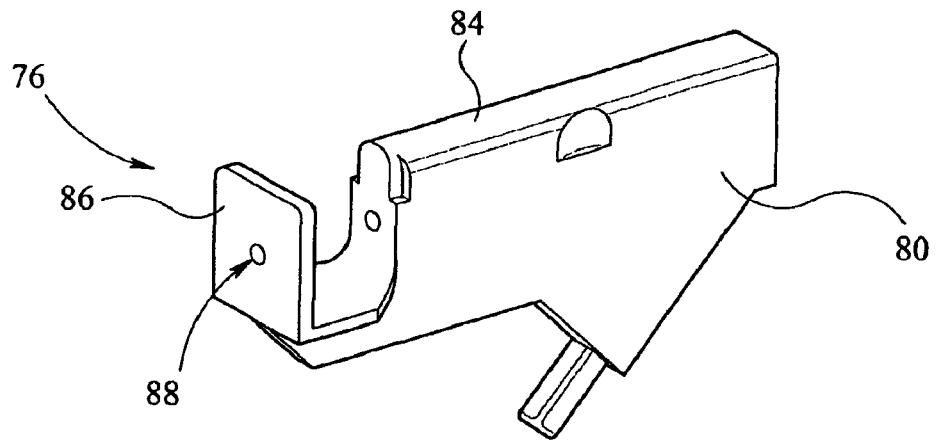
Figure 10:
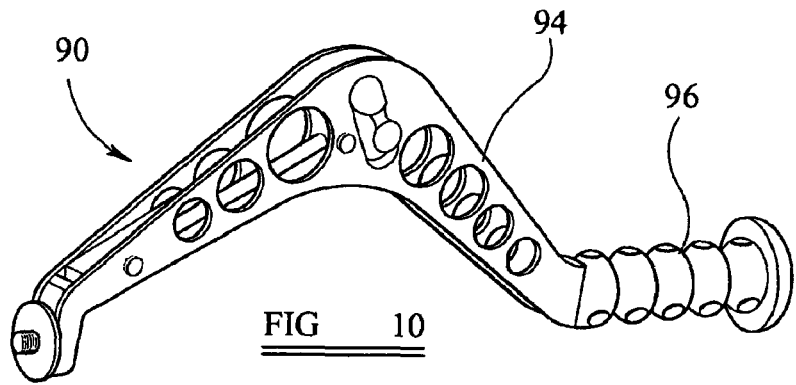
Figure 11:
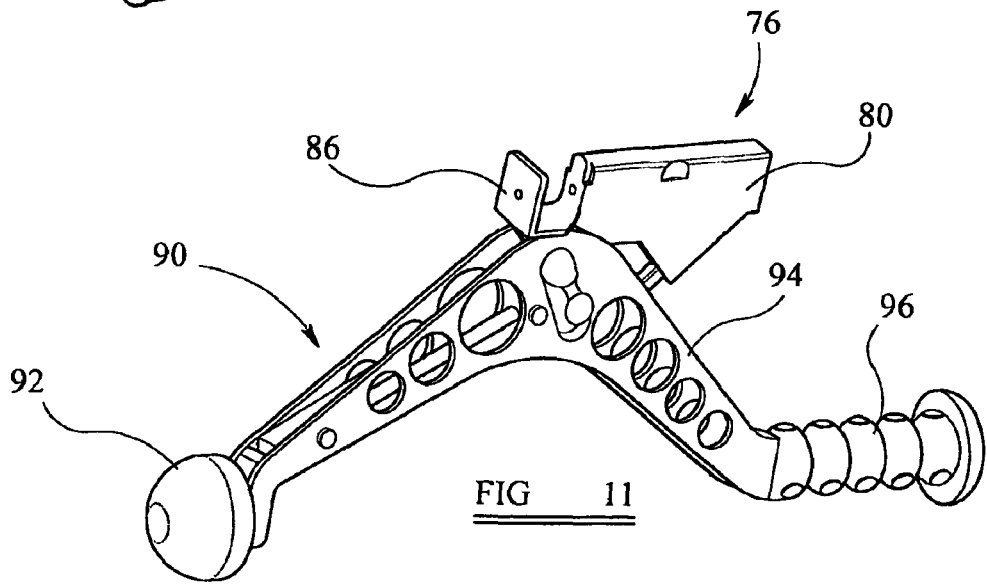

A positioning means 76 of an alignment device according to the present invention is illustrated in FIGS. 8 and 9. The positioning means 76 comprises a laser pointer 78 held in a mount 80 by a screw 82. A lid 84 is positioned over the laser pointer 78 to ensure sterile containment of the laser pointer 78. The mount 80 includes a target screen 86 held a fixed distance from the end of the laser pointer 78. An aperture 88 is provided through the centre of the target screen 86 to allow the laser beam from the laser pointer 78 to pass therethrough.

The positioning means 76 may be attached to an implant specific introducer 90 by the surgeon. In the embodiment illustrated in FIGS. 10 and 11, the introducer 90 is an acetabular cup insertion device. The surgeon also affixes an acetabular cup implant 92 to the end of the introducer 90. The cup 92 is arranged on the introducer 90 such that its convex exterior is exposed for positioning in a prepared acetabulum. The introducer 90 comprises an inverted V-shaped support 94 with a handle 96 provided at one end of the V and the cup 92 provided at the other. The positioning means 76 is mounted at the top of the V and is arranged such that the emitted laser beam is parallel to the line of axis of the cup 92 as it is held on the introducer 90.

Figure 12:
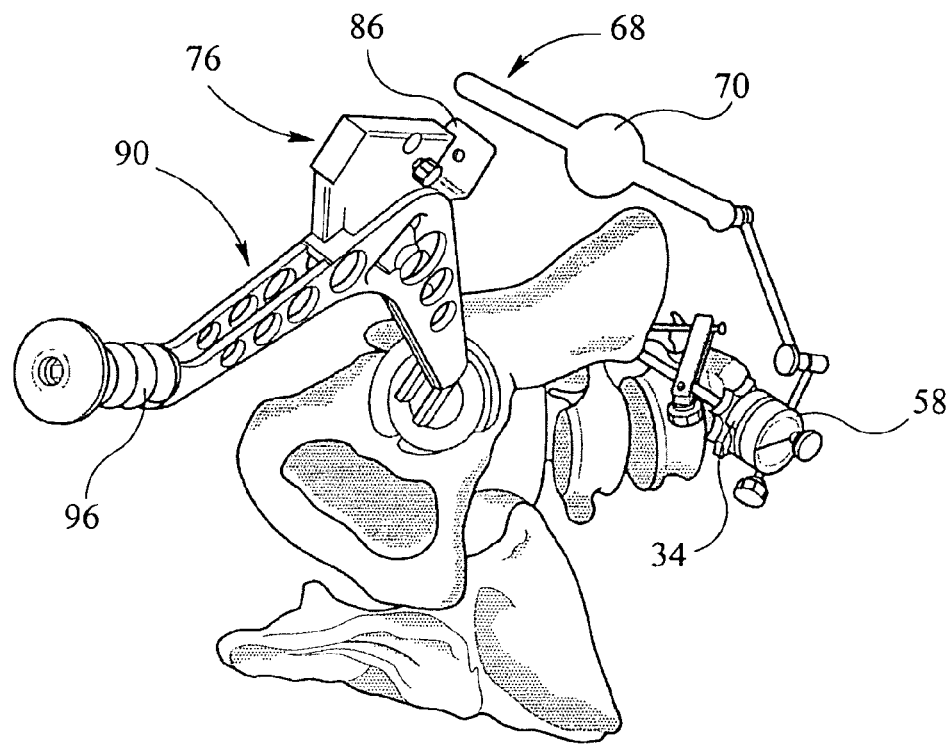

As shown in FIG. 12, the cup 92 attached to the introducer 90 is presented to the acetabulum, and the introducer 90 is inclined so that the laser beam hits the reflector 70 surface and retro-reflects onto the target screen 86 of the positioning means 76. Thus, when the incident beam and reflected beams are coincident (i.e. both pass through the aperture 88 of the target screen 86), the introducer 90 is perpendicular to the reflector 70. In this configuration, the cup implant 92 is positioned at a known attitude (i.e. that set by the guide assembly 54) with respect to the pelvic plane (in this case defined by the two anterosuperior iliac spines and the symphysis pubis).

FIG. 13 shows a partial side cross-sectional view illustrating the interface between the datum assembly 32 and the guide assembly 54. Thus, as can be seen, the guide marker 60 is a cylindrical component with a recess around the periphery of its upper surface configured to allow placement of an anteversion ring 56. Its lower surface is provided with a V-shaped projection 98 that slots into the V-shaped channel 36 in the swivel body 34 of the datum assembly 32.

Alternative and exploded views of several of the components described above are shown in FIG. 14 for clarity. Thus, as described in the above embodiment, the channel 36 of the swivel body 34 is V-shaped and includes three magnets 102 disposed in holes through its channel walls.

As also illustrated in FIG. 14, the couplings 43 and 47, disposed on the tops of the second and third rods 42 and 46, respectively, include cylindrical bores 110 orthogonally therethrough. A cylindrical shaft 107 is provided on the fourth rod 50 at the opposite end to the square cross-section 106. Accordingly, the cylindrical shaft 107 is free to rotate within the coupling 43 on the second rod 43. Similarly, a cylindrical shaft 112 is provided on the fifth rod 52 such that it is free to rotate within the coupling 47 on the third rod 46.

A screw 114 is provided with each of the couplings 43, 47 and 51 for clamping each of the rods 50, 52 and 50 extending through the respective bores 110, 110, 108 to thereby lock the framework in position.

The datum means framework may comprise magnetic components to simplify the framework assembly. The guide may also comprise magnetic components to simplify its construction. In addition, the guide may include a variable anteversion adjustment mechanism as opposed to interchangeable anteversion rings.

It will be appreciated by persons skilled in the art that various modifications may be, made to the above-described embodiments without departing from the scope of the present invention. For example, whilst the above discussion has been primarily concerned with the alignment of an acetabular component, the invention is equally applicable to the alignment of other prosthetic components as well as surgical tools such a cutting guides and reamers.

The invention claimed is:

1. An alignment device for use in a surgical procedure, comprising: a guide having a tangible guide component, said guide being configured for arranging the guide component at an angle with respect to a reference plane defined by two or more bony points, the guide component being pivotally mounted on an extension arm to facilitate rotation in a plane angled with respect to the reference plane; a datum means framework attached to the guide and comprising a datum assembly having a reference datum, the datum assembly being configurable to permit the reference datum to adopt the attitude of the reference plane and lockable in position, a remainder of the datum means framework being removable; and a positioning means; the positioning means and the guide component being operable to cooperate to position an item at the angle set by the guide component, the guide being configured for attachment to the reference datum to allow the guide component to be set relative to the reference datum, wherein one of the guide component and the positioning means comprises a laser pointer and the other of the guide component and the positioning means comprises a reflector.

2. An alignment device according to claim 1 wherein the tangible guide component defines a plane.

3. An alignment device according to claim 1 wherein the guide comprises an adjustment means for altering the set angle of the guide component.

4. An alignment device according to claim 3 wherein the adjustment means is constituted by an anteversion ring which defines an inclined surface relative to the reference element and which is configured for altering an anteversion angle and/or an inclination angle of the guide component.

5. An alignment device according to claim 4 wherein the inclined surface of the anteversion ring defines an anteversion angle of 20° and the anteversion ring is rotatable relative to the reference element to set the guide component at an inclination angle of 45°.

6. An alignment device according to claim 1 wherein the guide comprises a locking means to lock the angle of the guide component once it has been set.

7. An alignment device according to claim 1 wherein the positioning means is configured for attachment to an insertion tool.

8. An alignment device according to claim 7 wherein the positioning means is configured for attachment to the insertion tool such that the positioning means and insertion tool are thereafter held in a fixed relative disposition.

9. An alignment device according to claim 1 wherein the positioning means comprises an extendable portion to facilitate its cooperation with the guide component.

10. An alignment device according to claim 1 wherein a laser beam from the laser pointer is configured to emanate or pass through the centre of a target configured such that the reflected laser beam may be visible on the target to indicate that the reflector and laser pointer are not perpendicularly aligned.

11. An alignment device according to claim 1 wherein the guide component and the positioning means each comprise planar surfaces that can be placed against each other in order to cooperate by aligning one that is free to rotate with the other which is held at a fixed angle.

12. An alignment device according to claim 1 wherein the positioning means is arranged for positioning a cutting block or cutting blade.

13. An alignment device according to claim 1 wherein the positioning means is arranged for positioning a cutting block and the cutting block comprises a reflective surface that constitutes the positioning means.

14. An alignment device according to claim 1 wherein the positioning means is arranged for positioning a cutting blade and the cutting blade comprises a reflective surface that constitutes the positioning means.

\* \* \* \* \*